(12) United States Patent
Pomytkin et al.

(10) Patent No.: US 9,220,727 B2
(45) Date of Patent: Dec. 29, 2015

(54) METHOD OF DIETARY MANAGEMENT OF DEPRESSION

(71) Applicants: Igor Anatolyevich Pomytkin, Moscow (RU); Anton Sergeevich Chernopyatko, Moscow (RU)

(72) Inventors: Igor Anatolyevich Pomytkin, Moscow (RU); Anton Sergeevich Chernopyatko, Moscow (RU)

( * ) Notice: Subject to any disclaimer, the term of this patent is extended or adjusted under 35 U.S.C. 154(b) by 20 days.

(21) Appl. No.: 13/686,372

(22) Filed: Nov. 27, 2012

(65) Prior Publication Data

US 2013/0142883 A1    Jun. 6, 2013

(30) Foreign Application Priority Data

Dec. 5, 2011    (RU) ................. 2011149370

(51) Int. Cl.
| | |
|---|---|
| *A61K 47/00* | (2006.01) |
| *A61K 33/00* | (2006.01) |
| *A23L 2/52* | (2006.01) |
| *A23L 1/30* | (2006.01) |
| *A23L 1/29* | (2006.01) |

(52) U.S. Cl.
CPC ............... *A61K 33/00* (2013.01); *A23L 1/293* (2013.01); *A23L 1/30* (2013.01); *A23L 2/52* (2013.01); *A23V 2002/00* (2013.01)

(58) Field of Classification Search
USPC ....................................................... 424/439
See application file for complete search history.

(56) References Cited

U.S. PATENT DOCUMENTS

| | | | |
|---|---|---|---|
| 2003/0124201 A1 | 7/2003 | Bell | |
| 2008/0118463 A1* | 5/2008 | Pomytkin et al. | 424/85.2 |
| 2008/0292719 A1* | 11/2008 | Pomytkin et al. | 424/600 |

FOREIGN PATENT DOCUMENTS

| | | |
|---|---|---|
| EA | 012855 | 2/2008 |
| RU | 2270590 | 8/2004 |
| RU | 2390491 | 5/2007 |
| WO | WO 95/18545 | 7/1995 |
| WO | WO 03/049748 | 6/2003 |

OTHER PUBLICATIONS

Coppen et al, "Treatment of Depression: Time to Consider Folic Acid and Vitamin B12," Journal of Psychopharmacology, vol. 19, No. 1, pp. 59-65 (2005).*

Atlantis et al, Obesity Effects on Depression: Systematic Review of Epidemiological Studies, International Journal of Obesity, 32, No. 6, pp. 881-891 (2008).*

US Pharmacopeial Convention, Inc.; Water for Pharmaceutical Purposes; The US Pharmacopeia, The National Formulary; USP23, NF18, Supplement 5, Nov. 15, 1996, pp. 3547-3555.

Robertson, Michael I.; Regulatory issues with excipients; International Journal of Pharmaceuticals; 187 (1999) pp. 273-276.

Christensen, Robin et al.; Efficacy and safety of the weight-loss drug . . . ; Lancet 2007; vol. 370, Nov. 17, 2007, pp. 1706-1713.

Astrup, Arne et al.; Randomized Controlled Trials of the D1/D5 Antagonist Ecopipam . . . ; International Journal of Obesity, vol. 15, No. 7, Jul. 2007, pp. 1717-1731.

Rothman, L.S., et al.; The HITRAN molecular spectroscopic database: edition of 2000 including updates through 2001; Mar. 18, 2003; Journal of Quantitative Spectroscopy & Radiative Transfer; 82 (2003) 5-44.

American Psychiatric Association: Diagnostic and Statistical Manual of Mental Disorders, Fourth Edition. Washington, DC, American Phsychiatric Association, 1994; pp. 345-362.

Martinez, David, et ano.; Circadian rhythm sleep disorders; Indian J Med Res 131, Feb. 2010, pp. 141-149.

Rao, Uma, et al.; Heterogeneity in EEG sleep findings in adolescent depression: unipolar versus bipolar clinical course; Journal of Affective Disorders 70 (2002) pp. 273-280.

Claustrat, Bruno, et al.; A Chronobiological Study of Melatonin and Cortisol Secretion in Depressed Subjects: Plasma Melatonin, A Biochemical Marker in Major Depression; Biological Psychiatry, vol. 19, No. 8, 1984; pp. 1215-1228.

Dalton, E. Jane, et al.; Use of slow-release melatonin in treatment-resistant depression; Revue de psychiatrie et de neuroscience; vol. 25, No. 1, 2000, pp. 48-52.

Dolberg, Ornah T., et al.; Melatonin for the Treatment of Sleep Disturbances in Major Depressive Disorder; Am J Psychiatry 155L8, Aug. 1998, pp. 1119-1121.

* cited by examiner

*Primary Examiner* — Dennis J Parad
(74) *Attorney, Agent, or Firm* — Notaro, Michalos & Zaccaria P.C.

(57) ABSTRACT

The present invention relates to a method of the dietary management of depression, which method comprises a step of administering to a subject in need thereof a water containing from 0.0002 to 0.0278 molecular % of isotopologue HOD.

2 Claims, No Drawings

METHOD OF DIETARY MANAGEMENT OF DEPRESSION

FIELD OF THE INVENTION

The present invention is in the field of food industry and healthcare. More specifically, the present invention relates to medical foods for the dietary management of depression and anxiety.

BACKGROUND OF THE INVENTION

Depression is a disorder characterized by a combination of symptoms such as lowered mood, loss of energy, loss of interest, feeling of physical illness, poor concentration, altered appetite, altered sleep and a slowing down of physical and mental functions resulting in a relentless feeling of hopelessness, helplessness, guilt, and anxiety. Worldwide, depression is a major cause of disability and premature death. National Institute of Mental Health estimates prevalence of major depressive disorder (MDD) as 6.7% of U.S. adult population, 56.8% of those with disorders are receiving treatment. Average-age-of onset of MDD is estimated as of 32 years old. The exact cause of depression is not known. Present treatment of depression consists of psychotherapy, antidepressant drugs, or a combination of both. However, there are no special nutritional requirements related to the dietary management of patients with depression disorders.

A great number of depressions are also accompanied by anxiety. Up to 85% of those with major depression were also diagnosed with generalized anxiety disorder. Anxiety is a disorder characterized by a combination of symptoms such as fear, panic or anxiety in situations where most people would not feel anxious or threatened. National Institute of Mental Health estimates prevalence of anxiety disorders as 18.1% of U.S. adult population, 36.9% of those with disorder are receiving treatment. Anxiety and depression are linked. Both depression and anxiety are the reaction to stress and may share common molecular mechanisms. Present treatment of anxiety consists of antianxiety drugs. However, there are no special nutritional requirements related to the dietary management of patients with anxiety disorders.

Water is an essential nutrient. Total water intake includes drinking water, water in beverages, and water contained in food. The adequate intake for total water was set based on the median total water intake from U.S. survey data as 3.7 and 2.7 liters per day for men and women, respectively. Dietary Guidelines for Americans, 2005, U.S. Department of Health & Human Services. The natural water is a composition of nine water isotopologues ($H_2^{16}O$, $H_2^{17}O$, $H_2^{18}O$, $H^{16}OD$, $H^{17}OD$, $H^{18}OD$, $D_2^{16}O$, $D_2^{17}O$, $D^{18}O$) formed by stable isotopes of hydrogen (H and D) and oxygen ($^{16}O$, $^{17}O$, $^{18}O$), wherein content of major water isotopologue $H_2O$ ($H_2^{16}O$) is 99.7317 molecular % (mol. %) and major deuterium-containing isotopologue HOD ($H^{16}OD$) is 0.0311 mol. % (Vienna Standard Mean Ocean Water, VSMOW). Rothman et al., *J. Quant. Spectrosc. Radiat. Transfer*, 1998, 60, 665. Rothman et al., J. Quant. Spectrosc. Radiat. Transfer, 2003, 82, p. 9. Because of process of evaporation and condensation of ocean water, HOD levels in natural water slightly vary on Earth district. Only exclusion is natural water of Antarctica, which water contains HOD at levels of about 0.0178 mol. % (Standard Light Antarctic Precipitation, SLAP). A majority of people reside at Earth districts, where they consume natural water with HOD levels from 0.0280 to 0.0311 mol. %. On a calculation basis, when consume 2.7 and 3.7 liters of natural water per day, women and men consume no less than 0.8 and 1.0 ml of HOD as the obligate nutrient per day, respectively.

We discovered that HOD is a highly undesirable nutrient for a subject suffering from depression and/or anxiety and HOD restriction may represent a special medically determined nutrient requirement, the dietary management of which cannot be achieved by the modification of the normal diet alone. Surprisingly, we found that mammals are highly sensitive to HOD levels in drinking water and even change of HOD content in drinking water within the range of its natural concentrations provides a significant effect on susceptibility to psychosocial stress and predisposition to the development of anxiety and depression. Thus, the dietary management of depression and/or anxiety can be achieved by restriction of HOD daily consumption.

It is an object of the present invention is to provide a medical food for the dietary management of depression and/or anxiety comprising a water containing from 0.0002 to 0.0278 molecular % of isotopologue HOD.

It is an object of the present invention is to provide a method of the dietary management of depression and/or anxiety comprising a step of administering to a subject in need thereof the medical food of the invention.

It is an object of the present invention is to provide a method of the treatment of depression in a subject in need thereof comprising steps of: (a) administering to the subject an antidepressant drug, and (b) administering to the subject the medical food of the invention.

It is an object of the present invention is to provide a method of the treatment of anxiety in a subject in need thereof comprising steps of: (a) administering to the subject an antianxiety drug, and (b) administering to the subject the medical food of the invention.

DETAILED DESCRIPTION OF THE INVENTION

The present invention provides a medical food for the dietary management of depression and/or anxiety comprising a water containing from 0.0002 to 0.0278 molecular % of isotopologue HOD.

In a preferred embodiment of the invention, the medical food comprises water containing from 0.0178 to 0.0278 molecular % of isotopologue HOD.

As used herein, the term "medical food" refers to a food which is formulated to be consumed or administered enterally under the supervision of a physician and which is intended for the specific dietary management of depression and/or anxiety, for which distinctive nutritional requirements, based on recognized scientific principles, are established by medical evaluation.

In a preferred embodiment of the invention, the medical food is specially formulated and processed as a drink product. Such drink products include, but are not limited by, drinking water, beverage, and liquid food.

As used herein, the term "depression" refers to a mental disorder typically characterized by a lasting sad mood and/or loss of interest or pleasure in most activities. Examples of depression disorders include, but are not limited to: major depressive disorder also known as major depression, unipolar disorder, or clinical depression; major depressive episode; atypical depression; depression (mood); melancholic depression; psychotic depression; elderly depression; psychosocial stress-related depression; and postpartum depression.

As used herein, the term "anxiety" refers to an anxiety disorder or condition. Examples of anxiety disorders include, but are not limited to: panic attack; agoraphobia; acute stress disorder; specific phobia; panic disorder; psychoactive substance anxiety disorder; organic anxiety disorder; obsessive-compulsive anxiety disorder; posttraumatic stress disorder; generalized anxiety disorder; and anxiety disorder NOS.

As used herein, the term "isotopologue" is in accordance with IUPAC Compendium of Chemical Terminology 2nd Edition (1997) and refers to a molecular entity that differs only in isotopic composition (number of isotopic substitutions). Examples of such isotopologues include $H_2^{16}O$, $H_2^{17}O$, $H_2^{18}O$, $H^{16}OD$, $H^{17}OD$, $^1H^{18}OD$, $D_2^{16}O$, $D_2^{17}O$, and $D_2^{18}O$. The isotopologue $H^{16}OD$ is indicated in the present invention as HOD.

In preferred embodiments of the invention, HOD content in the water can be determined by methods well-known from the art. HOD levels can be directly measured by laser spectrometry. *R. Van Trigt. R. van Trigt. Laser Spectrometry for Stable Isotope Analysis of Water Biomedical and Paleoclimatological Applications*. 2002, *Groningen: University Library Groningen*. Also, HOD levels can be determined by conventional isotope mass-spectrometry as D/H ratio and re-calculated to HOD contents given that content of other deuterium-containing isotopologues in water is negligible as compared to HOD. For the reference, VSMOW water contains 0.00006 mol. % $H^{18}OD$; 0.00001 mol. % $H^{17}OD$; and less than 0.00001 mol. % for sum of isotopologues $D_2^{16}O$, $D_2^{17}O$, and $D_2^{18}O$. The range 0.0002 to 0.0278 mol. % of isotopologue HOD in the water of the invention corresponds to the range of D/H ratio 1 to 139 ppm. The range 0.0178 to 0.0278 mol. % of isotopologue HOD in the water of the invention corresponds to the range of deuterium content 89 to 139 ppm.

In preferred embodiments of the invention, the water containing 0.0002 to 0.0278 mol. % of isotopologue HOD can be prepared by a variety of industrial procedures well-known from the art, e.g. vacuum distillation of natural water. The water containing 0.0178 to 0.0278 mol. % of isotopologue HOD can be obtained from rare natural sources (e.g. Antarctic precipitations) or prepared by a variety of industrial procedures well-known from the art, e.g. vacuum distillation of natural water.

In practicing the invention, the water containing 0.0002 to 0.0278 mol. % of isotopologue HOD may contain other water isotopologues at levels equal or other than in VSMOW standard of natural water, e.g. $0<H_2^{18}O\leq0.2000$ mol. %; $0<H_2^{17}O\leq0.0370$ mol. %; $0<H^{17}OD\leq0.0270$ mol. %; $0<H^{18}OD\leq0.0270$ mol. %; $0<D_2^{16}O\leq0.0270$ mol. %; $0<D_2^{17}O\leq0.0270$ mol. %; $0<D_2^{18}O\leq0.0270$ mol. %, and $0<H_2^{16}O\leq99.9998$ mol. %.

The medical food of the invention may be prepared by well-known procedures using well-known optional ingredients. Such optional ingredients generally are used individually at levels from about 0.0005% to about 10.0%, preferably from about 0.005% to about 1.0% by weight of the composition. Examples of suitable optional ingredients include, but are not limited to, buffers, sweeteners, colorants, carriers, and etc.

In the preferred embodiments of the invention, the medical food is a liquid medical food specially formulated and manufactured in form of drinking water or beverage. The liquid medical food may be prepared by saturation of water containing 0.0002 to 0.0278 mol. % of isotopologue HOD with carbon dioxide or/and inorganic salts typically abandoned in natural drinking water. The examples of such salts include, but are not limited to, sodium chloride, sodium bicarbonate, calcium chloride, magnesium sulfate, etc.

Further, the present invention provides a method of the dietary management of depression and/or anxiety comprising a step of administering to a subject in need thereof the medical food of the invention.

In practicing the method of the invention, the medical food can be administered orally for a period of one day or longer and in amounts as prescribed by a physician which manages the diet and/or provides medical supervision.

In practicing the method of the invention, the medical food may be formulated as the drinking water or beverage that can be administered in amounts from 0.1 to 4.0 liters per subject per day.

Further, the present invention provides a method of the treatment of depression in a subject in need thereof comprising steps of: (a) administering to the subject an antidepressant drug, and (b) administering to the subject the medical food of the invention.

As used herein, the term "antidepressant drug" refers to drugs used to treat depression. Such drugs include without limitation: tricyclic antidepressants, such as clomipramine, amoxapine, nortriptyline, moprotilene, trimipramine, imipramine, or protriptyline; monoamine oxidase inhibitors; serotonin reuptake inhibitors, including selective serotonin reuptake inhibitors, such as citalopram, escitalopram, duloxetine, fluoxetine, sertraline, norsertraline, paroxetine, mirtrazepine, fluvoxamine, milnacipran, clominpramine, femoxetine, indapline, alaprolclate, cericlamine, or ifoxetine; norepinephrine reuptake inhibitors, including selective norepinephrine reuptake inhibitors, such as desipramine, maprotiline, lofepramine, reboxetine, oxaprotiline, fezolamine, tomoxetine, or (S,S)-hydroxybupropion; dopamine reuptake inhibitors, such as amineptine, bupropion, and venlafaxine; and atypical antidepressants, such as venlafaxine, nefazodone, or trazodone; therapeutically active isomers or metabolites of any of the foregoing; and pharmaceutically acceptable salts, solvates, clathrates, polymorphs, or co-crystals of any one of the foregoing.

In practicing the method of the invention, the antidepressant drug is administered as prescribed by the physician.

Further, the present invention provides a method of the treatment of anxiety in a subject in need thereof comprising steps of: (a) administering to the subject an antianxiety drug, and (b) administering to the subject the medical food of the invention.

As used herein, the term "antianxiety drug" refers to drugs used to treat anxiety. Such drugs include without limitation: clonazepam, alprazolam, lorazepam, clorazepate, oxazepam, flurazepam, diazepam, halazepam, prazepam, chlordiazepoxide, buspirone, gepirone, tandospirone, ipsapirone, bentazepam, citalopram, clobazam, clotiazepam, etifoxine, etizolam, delorazepam, ethyl loflazepate, flutazolam, fluoxetine, flutoprazepam, ketazolam, metaclazepam, mexazolam, moclobemide, oxazolam, tofisopam, pinazepam, paroxetine, pivagabine, rilmazafone, sertraline, tianeptine, venlafaxine, zotepine, escitalopram, fluvoxamine, pregabalin, agomelatine, duloxetine, ocinaplon, pagoclone, aprepitant, dexmedetomidine, eglumegad, eplivanserin, vestipitant, levetiracetam, olanzapine, tiagabine, emapunil, dextofisopam, itriglumide, S-desmethylzopiclone, gabapentin, opipramol, sumatriptan, and nefazodone; therapeutically active isomers or metabolites of any of the foregoing; and pharmaceutically acceptable salts, solvates, clathrates, polymorphs, or co-crystals of any one of the foregoing.

In practicing the method of the invention, the antianxiety drug is administered as prescribed by the physician.

As used herein, the term "subject" refers to any mammal. Nonexclusive examples of such mammals include, but are not limited to, animals such as a dog, a cat, a horse, and a human. Preferably, the subject is a human.

The following examples are presented to demonstrate the invention. The examples are illustrative only and are not intended to limit the scope of the invention in any way.

Example 1

This example demonstrates the preparation of water samples with different contents of isotopologue HOD. The samples were prepared by mixing in certain proportions the conventional distilled water containing 0.0300 mol. % HOD and water containing 0.0002 mol. % HOD, wherein the last water was prepared by high-effective vacuum distillation of the conventional distilled water at 60° C. and pressure 0.2 bars using the distillation column of 10 m of height. HOD levels were measured by isotope laser spectroscopy using Los Gatos Research (LGR) Liquid Water Isotope Analyzer. Table 1 shows water samples comprising 0.0002 to 0.0278 mol. % of isotopologue HOD and D/H ratios corresponding therewith.

TABLE 1

Water samples

| Sample | HOD content, mol. % | D/H ratio, ppm |
|---|---|---|
| Water No 1 | 0.0278 | 139 |
| Water No 2 | 0.0240 | 120 |
| Water No 3 | 0.0178 | 89 |
| Water No 4 | 0.0002 | 1 |

Example 2

This example demonstrates the medical food for the dietary management of depression and anxiety. The medical foods were formulated as mineralized drinking waters with HOD content as indicated in Table 2.

TABLE 2

Medical foods

| Ingredient (HOD, mol. %) | Content, wt. % |
|---|---|
| Medical food 1 | |
| Water No 1 (0.0278) | 99.953 |
| Calcium Chloride | 0.015 |
| Magnesium Chloride | 0.007 |
| Sodium Bicarbonate | 0.025 |
| Medical food 2 | |
| Water No 2 (0.0240) | 99.953 |
| Calcium Chloride | 0.015 |
| Magnesium Chloride | 0.007 |
| Sodium Bicarbonate | 0.025 |
| Medical food 3 | |
| Water No 3 (0.0178) | 99.953 |
| Calcium Chloride | 0.015 |
| Magnesium Chloride | 0.007 |
| Sodium Bicarbonate | 0.025 |
| Medical food 4 | |
| Water No 4 (0.0002) | 99.953 |
| Calcium Chloride | 0.015 |
| Magnesium Chloride | 0.007 |
| Sodium Bicarbonate | 0.025 |

The medical foods No 1 through 4 were prepared by dissolution of Calcium Chloride, Magnesium Chloride, and Sodium Bicarbonate in Waters No 1 through 4, respectively, and subsequent bottling in bottles of 330 ml volume.

Example 3

This example shows that deuterium-containing isotopologue HOD dose-dependently predisposes to the development of depression. Water samples of Table 3 were prepared by mixing in certain proportions of two equally mineralized waters having HOD level of 0.0184 mol. % (D/H ratio=92 ppm) and HOD level 0.0282 mol. % (D/H ratio=141 ppm).

TABLE 3

Water samples

| Water sample | HOD content, mol. % | D/H ratio, ppm |
|---|---|---|
| W1 | 0.0184 | 92 |
| W2 | 0.0240 | 120 |
| W3 | 0.0258 | 129 |
| W4 | 0.0282 | 141 |

Three-months-old male C57Bl/6 mice were randomly assigned by 15 animals per group and received W1, W2, W3, and W4 (Table 3) as drinking waters ad libitum for 14 days and then were tested for depressive-like behavior in a forced swim test and novel cage test, commonly accepted paradigms for pre-clinical testing of a depressive-like behavior. Antidepressant Imipramine (15 mg/kg per day) was administered to mice that were taken as positive control in the test. Results of forced swim test are presented in Table 4 as mean±SEM latency to floating (Latency) and duration of floating (Duration). As shown in Table 4, the increase in HOD levels in drinking water results in significant decrease in the latency to floating and increase in the duration of floating, meaning that deuterium-containing isotopologue HOD predisposes to the development of depression.

TABLE 4

Forced swim test

| Sample (HOD, mol. %) | Latency, s | Duration, s |
|---|---|---|
| W1 (0.0184) | 46 ± 6[#] | 89 ± 15[#] |
| W2 (0.0240) | 48 ± 9[#] | 80 ± 14[#] |
| W3 (0.0258) | 47 ± 11 | 86 ± 19[#] |
| W4 (0.0282) | 31 ± 6* | 128 ± 12* |
| Imipramine | 58 ± 4*[#] | 79 ± 8[#]* |

*Differs significantly of W1 ($p < 0.05$).
[#]Differs significantly of W4 ($p < 0.05$).

Results of novel cage test are presented in Table 5 as mean±SEM number of exploratory rearings in the new cage. As found, the increase in HOD levels in drinking water results in significant decrease in the number of exploratory rearings in the new cage, meaning that deuterium-containing isotopologue HOD predisposes to the development of depression.

TABLE 5

Novel cage test

| Sample (HOD, mol. %) | Number, n |
|---|---|
| W1 (0.0184) | 35.0 ± 1.5[#] |
| W2 (0.0240) | 35.5 ± 1.5[#] |
| W3 (0.0258) | 33.0 ± 1.5 |

TABLE 5-continued

Novel cage test

| Sample (HOD, mol. %) | Number, n |
|---|---|
| W4 (0.0282) | 30.0 ± 1.0* |
| Imipramine | 34.0 ± 1.5# |

*Differs significantly of W1 (p < 0.05).
Differs significantly of W4 (p < 0.05).

Thus, these results suggest that deuterium-containing water isotopologue HOD in drinking water predisposes to depressive-like behavior. Therefore, HOD is a very undesirable nutrient for subjects with depressive disorders and HOD restriction may represent a special medically determined nutrient requirement, the dietary management of which cannot be achieved by the modification of the normal diet alone.

Example 4

This example demonstrates that deuterium-containing isotopologue HOD predisposes to the development of anhedonia, the core symptom of depression. Young adult male C57Bl/6J mice received ad libitum waters W1 or W4 (Table 3) for one week prior the onset of stress and during the ten days of a chronic stress. Citalopram 15 mg/kg per day per os was used as the reference antidepressant drug. There was no difference between groups at baseline. At 10th day of the stress procedure, animals were tested on the sucrose preference, common test for assessment of anhedonia. Results are presented in Table 6 as mean±SEM percent of sucrose preference.

TABLE 6

Sucrose preference test

| Group (HOD, mol.%) | Sucrose preference, % |
|---|---|
| W1 (0.0184) | 73.5 ± 3.0# |
| W4 (0.0282) | 62.5 ± 2.0* |
| Citalopram | 70.0 ± 3.0# |

*Differs significantly of W1 (p < 0.05).
Differs significantly of W4 (p < 0.05).

As shown in Table 6, the increase in HOD levels in drinking water results in significant decrease in sucrose preference, meaning that deuterium-containing isotopologue HOD predisposes to the development of anhedonia, the core symptom of depression. Therefore, HOD is a very undesirable nutrient for subjects with depressive disorders and HOD restriction may represent a special medically determined nutrient requirement, the dietary management of which cannot be achieved by the modification of the normal diet alone.

Example 5

This example demonstrates that deuterium-containing isotopologue HOD predisposes to the development of depression in elderly. Table 7 shows that sucrose preference in old C5Bl/6J mice is significantly decreased in comparison with young adult C5Bl/6J mice, meaning that normal aging induces spontaneous anhedonia in mice.

TABLE 7

| Group | Sucrose preference, % |
|---|---|
| Young adult C57Bl/6J mice (3 months old) | 78.0 ± 2.5 |
| Old C57Bl/6J mice (18 months old) | 60.6 ± 3.1* |

*Differs significantly of young adult mice (p < 0.05).

To estimate effect of HOD on anhedonia in elderly, 18 month old male C57Bl/6J mice received ad libitum waters W1 or W4 (Table 3) for 14 days. There was no difference between groups at baseline. At the end of the experiment, mice were tested in sucrose preference test. Results are presented in Table 8 as mean±SEM percent of sucrose preference. As found, the increase in HOD levels in drinking water results in significant decrease in sucrose preference, meaning that deuterium-containing isotopologue HOD predisposes to the development of anhedonia, the core symptom of depression, in elderly.

TABLE 8

Sucrose preference test

| Group (HOD, mol. %) | Sucrose preference, % |
|---|---|
| W1 (0.0184) | 81.3 ± 1.9 |
| W4 (0.0282) | 69.4 ± 4.4* |

*Differs significantly of W1 (p < 0.05).

To estimate effect of HOD on depressive-like behavior in elderly, 18 month old male C57Bl/6J mice received ad libitum waters W1 or W4 (Table 3) for 14 days. There was no difference between groups at baseline. At the end of the experiment, mice were tested in forced swim test. Results are presented in Table 9 as mean±SEM of latency to floating (Latency) and duration of floating (Duration). As found, the increase in HOD levels in drinking water results in decrease in the latency to floating and significant increase in the duration of floating, meaning that deuterium-containing isotopologue HOD predisposes to the development of depression in elderly.

TABLE 9

Forced swim test

| Group (HOD, mol. %) | Latency, s | Duration, s |
|---|---|---|
| W1 (0.0184) | 17.4 ± 4.2 | 126.7 ± 13.9 |
| W4 (0.0282) | 13.7 ± 3.1 | 186.7 ± 10.0* |

*Differs significantly of W1 (p < 0.05).

Therefore, HOD is a very undesirable nutrient for elderly subjects with depressive disorders and HOD restriction may represent a special medically determined nutrient requirement, the dietary management of which cannot be achieved by the modification of the normal diet alone.

Example 6

This example demonstrates that deuterium-containing isotopologue HOD dose-dependently predisposes to the development of anxiety. Three-months-old male C57Bl/6 mice were randomly assigned by 15 mice per group and received W1, W2, W3, and W4 (Table 3) as drinking waters ad libitum for 14 days and then were tested for anxiety-like behavior in a dark-light box test, commonly accepted paradigm for preclinical testing of anxiolytic effects. Bolus injection of anxiolytic drug Diazepam (2.5 mg/kg, 30 min prior the test) was used as a positive reference control. Results are presented in Table 10 as mean±SEM time spent in the lit box (Time).

TABLE 10

Dark-light box test

| Sample (HOD, mol. %) | Time, s |
|---|---|
| W1 (0.0184) | 99.6 ± 6.0# |
| W2 (0.0240) | 104.7 ± 6.4# |
| W3 (0.0258) | 95.7 ± 10.3# |
| W4 (0.0282) | 75.0 ± 7.8* |
| Diazepam | 155.2 ± 7.8*# |

*Differs significantly of W1 (p < 0.05).
Differs significantly of W4 (p < 0.05).

As shown in Table 10, the increase in HOD levels in drinking water results in significant decrease in the time spent in the lit box, meaning that deuterium-containing isotopologue HOD predisposes to the development of anxiety. Therefore, HOD is a very undesirable nutrient for subjects with anxiety disorders and HOD restriction may represent a special medically determined nutrient requirement, the dietary management of which cannot be achieved by the modification of the normal diet alone.

Example 7

This example demonstrates the method of the treatment of depression by administering antidepressant and the water depleted in HOD isotopologue. Antidepressant imipramine was administered per os at doses 2.5 mg/kg (suboptimal) and 15 mg/kg per day (optimal) for 14 days to young adult male C57Bl/6J mice receiving W2 or W4 (Table 3) as drinking waters ad libitum. Then, forced swim test and object recognition memory test were performed to assess effect of HOD on therapeutic effect of Imipramine and side effect of Imipramine, respectively. Results of forced swim test are presented in Table 11 as mean±SEM duration of floating on first day and second day of testing in comparison with non-treated control. Table 11 shows that imipramine significantly decreases duration of floating in optimal dose 15 mg/kg, independent on HOD content in drinking water. There is a trend (p<0.15) toward decreasing of floating duration in mice receiving less HOD with drinking water during the course of imipramine treatment in its suboptimal dose of 2.5 mg/kg. These results suggest that lowering HOD levels in drinking water favors therapeutic effects of the antidepressant taken in its suboptimal dose.

TABLE 11

Forced swim test

| Group (HOD, mol. %) | Duration 1st day, s | Duration 2nd day, s |
|---|---|---|
| Control | 173 ± 7 | 221 ± 10 |
| Imi 2.5 mg/kg + W2 (0.0240) | 182 ± 10 | 219 ± 9 |
| Imi 2.5 mg/kg + W4 (0.0282) | 158 ± 11 | 189 ± 11 |
| Imi 15.0 mg/kg + W2 (0.0240) | 113 ± 15* | 162 ± 20* |
| Imi 15.0 mg/kg + W4 (0.0282) | 98 ± 13* | 167 ± 9* |

*Differs significantly of control (p < 0.05).

The object recognition memory test was performed as follows: mice were placed to an observation chamber that represented itself a glass cylinder (Ø 25 cm, height 35 cm, illumination intensity 5 Lux). Under sound-proof conditions, their parameters of the exploration of two identical objects (a taste-free and smell-free toy 6 cm×3 cm×2.5 cm) were scored: 1) a latency of exploration and 2) a total duration of exploratory behavior during 15 min (for each object and a sum). The absolute measures which were registered on the Day 1 of the test were taken as parameters of neophobia and exploration of novelty (a sum of exploration of two objects), respectively. The test was repeated on the Day 2, where under identical testing conditions, the object at the position where the exploration was app. 50% lesser than at another location (presumably because it was more distanced from the wall 40 cm vs. 20 for another object, and closer to the experimenter), was replaced with a new object of similar size and texture (3 cm×6 cm×3 cm). On each day, preferences for the exploration between two objects were expressed in percent as time spent in exploration of either object derived to the total duration of exploratory behavior. Elevated object exploration at non-preferred position on Day 2 was considered as a manifestation of retained memory for the "old" object, therefore a newly placed object was recognized as novel one and therefore explored more. Each group constituted 10 mice. Results of the test are presented in Table 12 as mean±SEM percent of preference for new object placed in non-preferred area (Preference, %).

TABLE 12

Object recognition memory test

| Group (HOD, mol. %) | Preference, % |
|---|---|
| Control | 53 ± 4 |
| Imipramine 15.0 mg/kg + W2 (0.0240) | 52 ± 4 |
| Imipramine 15.0 mg/kg + W4 (0.0282) | 40 ± 3*# |

*Differs significantly of control (p < 0.05).
Differs significantly of Imipramine 15.0 mg/kg + W2 (p < 0.05).

There was no difference between groups in initial preference to an object in non-preferred area, meaning treatment did not interfere with exploration of novel object per se under employed conditions. There was a significant difference between groups to a new object placed in non-preferred area. Control mice showed higher than 50% preference to a novel object that was placed to a non-preferred area, thus, showing that that recognized this object as a different from a former one. Imipramine plus W4 water-treated mice displayed memory impairment, since they showed no such increase in preference in exploring of a new object. Their preference to explore this object was significantly lower than in control group of mice (p=0.02, unpaired t-test, respectively). Imipramine plus W2 water-treated mice displayed no memory impairment. These results suggest that drinking water depleted in HOD during a course of imipramine treatment significantly reduces imipramine-induced side effects, e.g. memory impairments. Therefore, administering to a subject the medical food, e.g. drinking water, depleted in HOD isotopologue favors to the treatment of depression during the course of treatment with antidepressants.

Example 8

This example demonstrates the method of the treatment of anxiety by administering anxiolytic drug and the water depleted in HOD isotopologue. Male BALB/c mice received W2 or W4 (Table 3) as drinking waters ad libitum for 14 days or conventional laboratory water as control. Anxiolytic drug diazepam was injected in its suboptimal dose of 0.3 mg/kg to mice from W2 and W4 groups 30 min prior the dark-light box test, commonly accepted paradigm for pre-clinical testing of anxiolytic effects. Results are presented in Table 13 as mean±SEM time spent in the lit box (Time).

TABLE 13

| Dark-light box test | |
|---|---|
| Group (HOD, mol. %) | Time, s |
| Control | 34 ± 11 |
| Diazepam + W2 (0.0240) | 82 ± 10* |
| Diazepam + W4 (0.0282) | 62 ± 11 |

*Differs significantly of control (p < 0.05).

As shown, diazepam in its suboptimal dose non-significantly increases time spent in lit box in W4 group as compared to the control. However, diazepam significantly increases time spent in lit box in W2 group, wherein mice consume less HOD with drinking water than in W4 group. Therefore, administering to a subject the medical food, e.g. drinking water, depleted in HOD isotopologue favors to the treatment of anxiety during the course of treatment with anxiolytic drugs.

We claim:

1. A method of the dietary management of major depressive disorder consisting of administering to a subject in need thereof a water, in which HOD isotopologue is present in concentration of from 0.0010 to 0.0278 molecular %.

2. The method of claim 1, wherein the HOD isotopologue is present in concentration of from 0.0178 to 0.0278 molecular %.

* * * * *